United States Patent [19]

Akopov et al.

[11] Patent Number: 5,242,457
[45] Date of Patent: Sep. 7, 1993

[54] SURGICAL INSTRUMENT AND STAPLES FOR APPLYING PURSE STRING SUTURES

[75] Inventors: Ernest Akopov; Vyacheslav Astashev; Anatoly Ramm; Alexandr Reztsov, all of Moscow, U.S.S.R.

[73] Assignee: Ethicon, Inc., Somerville, N.J.

[21] Appl. No.: 881,010

[22] Filed: May 8, 1992

[51] Int. Cl.⁵ .......................................... A61B 17/00
[52] U.S. Cl. ................................. 606/144; 606/139; 606/148; 606/151; 606/219; 606/220; 227/175; 227/176; 227/178; 227/902
[58] Field of Search ............... 606/75, 148, 219, 220, 606/144, 151; 227/175-178, 19, 181, 902; 24/533, 534; 411/457, 458, 473, 456, 471, 459-464, 472, 483, 485

[56] References Cited

U.S. PATENT DOCUMENTS

| | | | |
|---|---|---|---|
| 249,851 | 11/1881 | McGill | 411/483 |
| 266,652 | 10/1882 | Smith, Jr. | 411/461 |
| 325,115 | 8/1885 | Raymond | 411/457 |
| 350,507 | 10/1886 | Schulz | 411/457 |
| 366,555 | 6/1887 | Brewington | 411/483 |
| 433,894 | 8/1890 | Drendul | 411/457 |
| 569,648 | 10/1896 | Logan | 411/457 |
| 576,455 | 2/1897 | Johnson | 411/457 |
| 1,241,054 | 9/1917 | Tervo | 411/473 |
| 2,319,129 | 5/1943 | Hamilton | 411/457 |
| 2,390,219 | 12/1945 | La Place | 411/473 |
| 2,530,811 | 11/1950 | Cook | 411/473 |
| 3,339,448 | 9/1967 | McKee | 411/473 |
| 3,583,663 | 6/1971 | Snow, Jr. | 411/457 |
| 4,345,600 | 8/1982 | Rothfuss . | |
| 4,635,637 | 1/1987 | Schreiber | 606/219 |
| 4,749,114 | 6/1988 | Green | 227/19 |
| 4,773,420 | 9/1988 | Green . | |
| 4,821,939 | 4/1989 | Green | 227/19 |
| 4,915,107 | 4/1990 | Rebuffat et al. | 606/144 |
| 5,129,570 | 7/1992 | Schulze et al. | 227/19 |

FOREIGN PATENT DOCUMENTS 0725631 3/1955 United Kingdom ............... 411/457

Primary Examiner—Stephen C. Pellegrino
Assistant Examiner—Jeffrey A. Schmidt
Attorney, Agent, or Firm—Paul A. Coletti; Charles P. Boukus

[57] ABSTRACT

A surgical staple for securing a purse string suture to human tissue comprises a staple body of deformable material formed into a loop through which the purse string suture is threaded. The staple body includes a pair of legs which are deformable into an overlapping configuration upon insertion into the tissue to secure the staple body and the purse string suture to the tissue. Alternatively, the staple body includes two or more legs including barbed ends for anchoring the legs to the tissue. To secure the purse string suture, a plurality of staples is positioned about the periphery of the tubular section of tissue, the purse string suture is threaded through the loops in the staples, and the staples are driven into the tissue to secure the purse string suture thereto. In addition, a surgical instrument is provided for applying the staples and the purse string suture to the tissue. The instrument includes a pair of staple cartridges each having a row of staple receiving slots intersected by an elongated central slot which allows the purse string suture to be attached to the staples in the cartridge prior to the operation of the instrument.

17 Claims, 10 Drawing Sheets

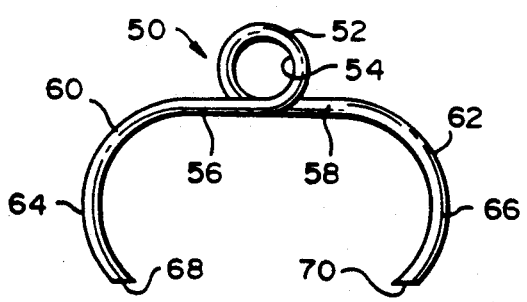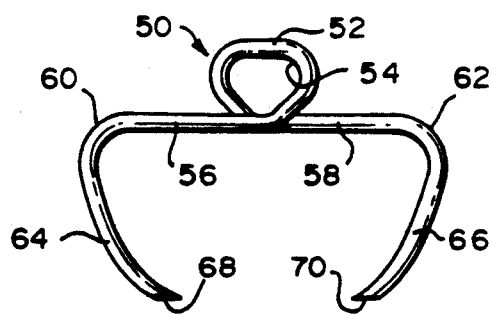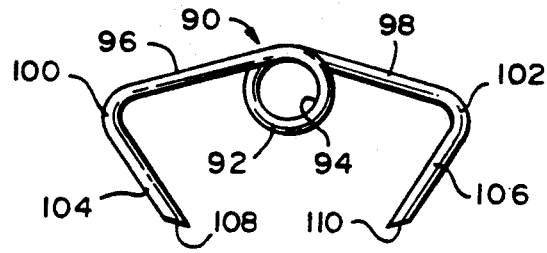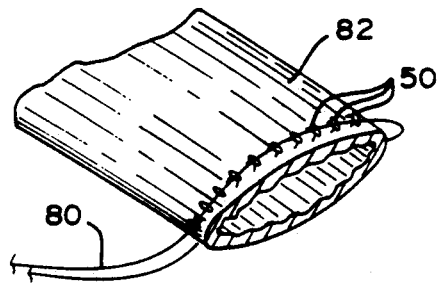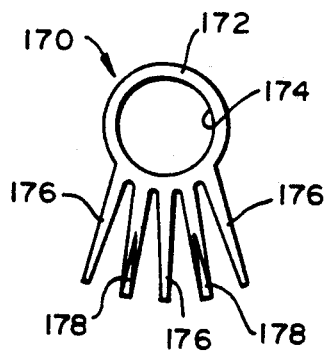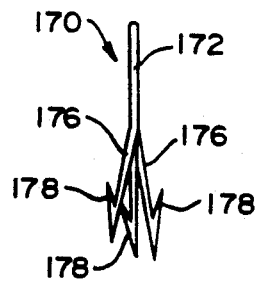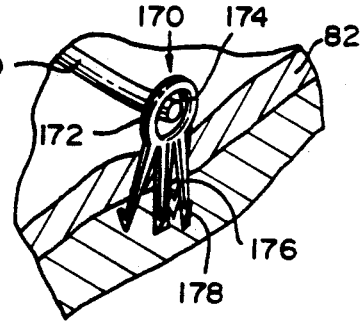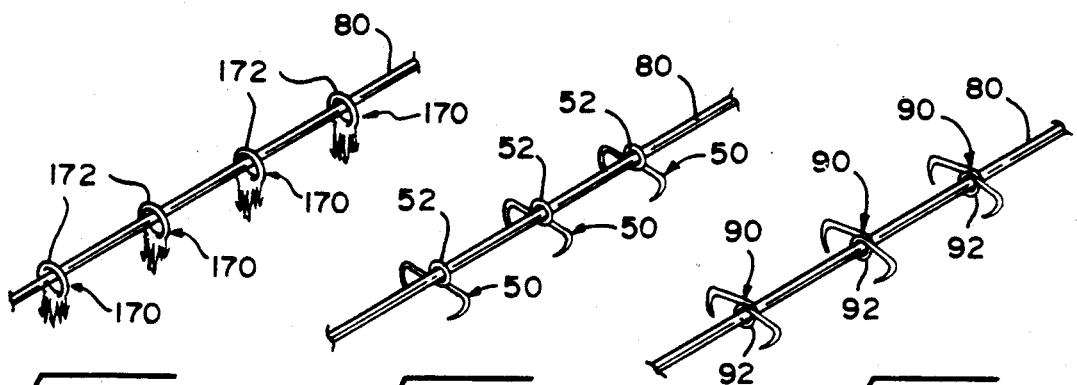

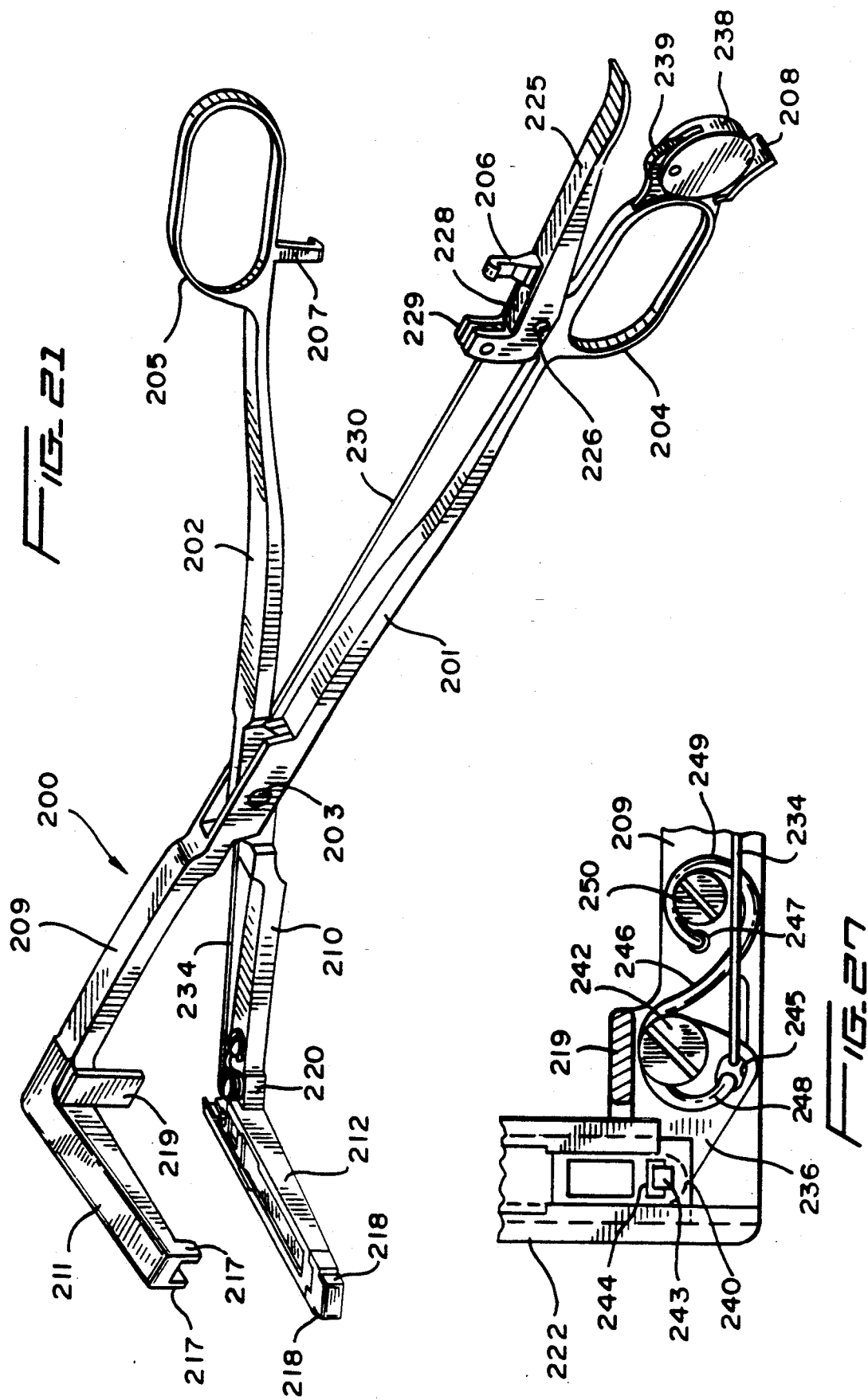

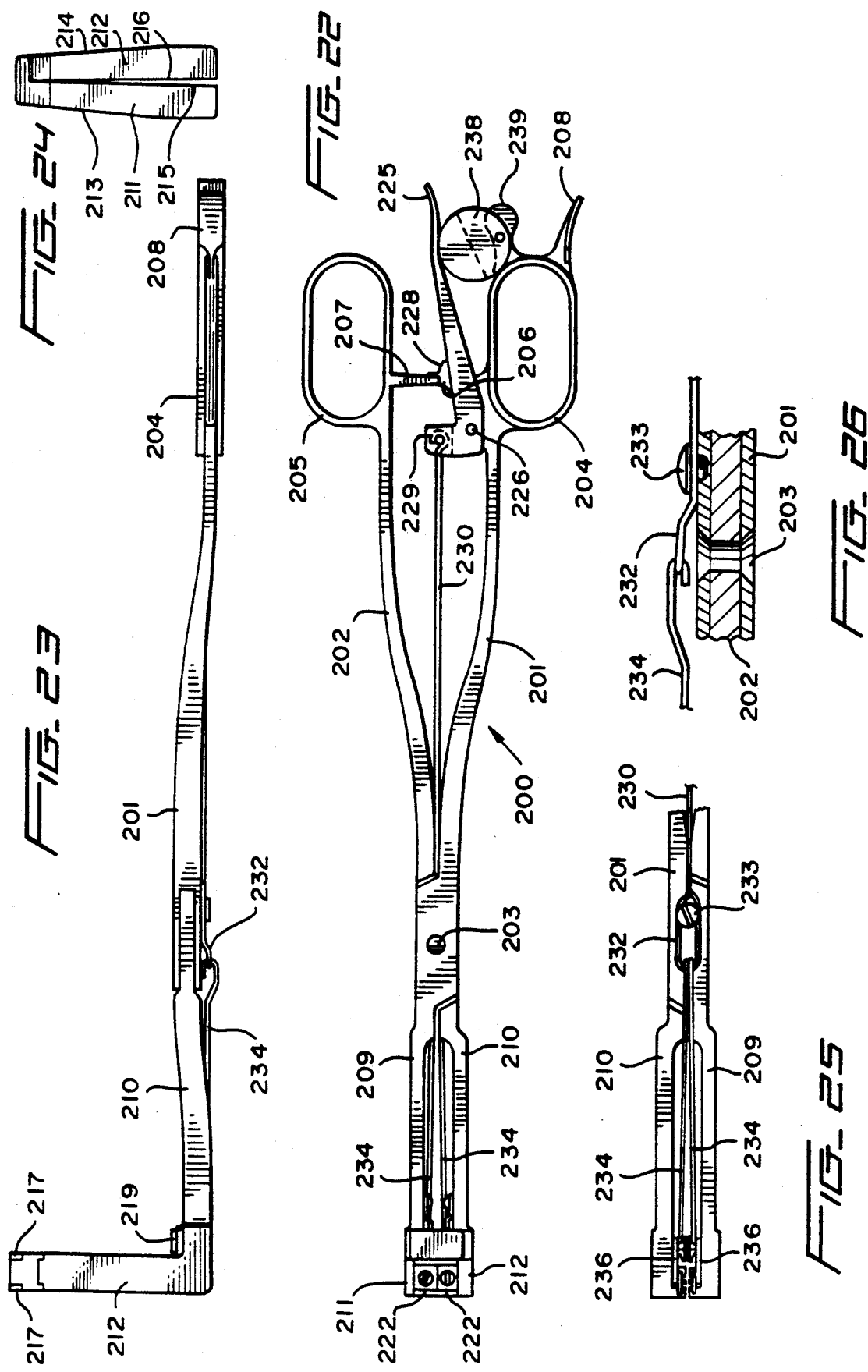

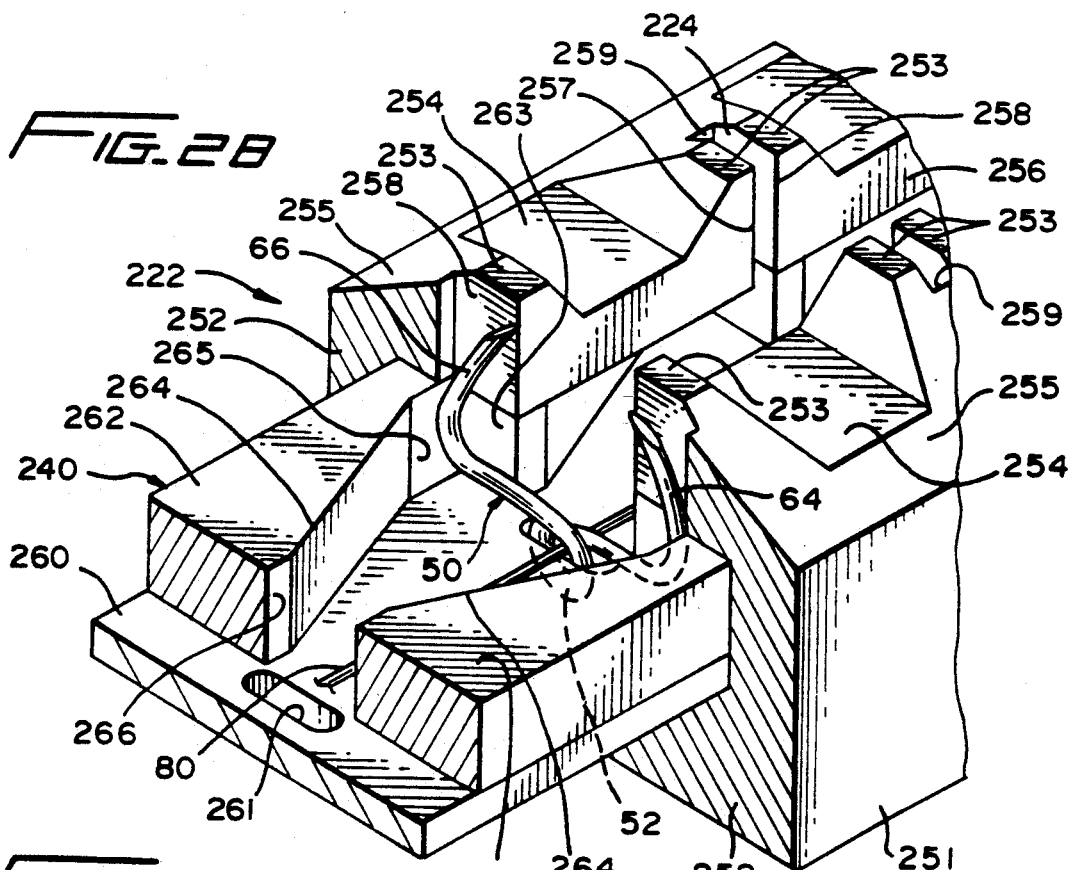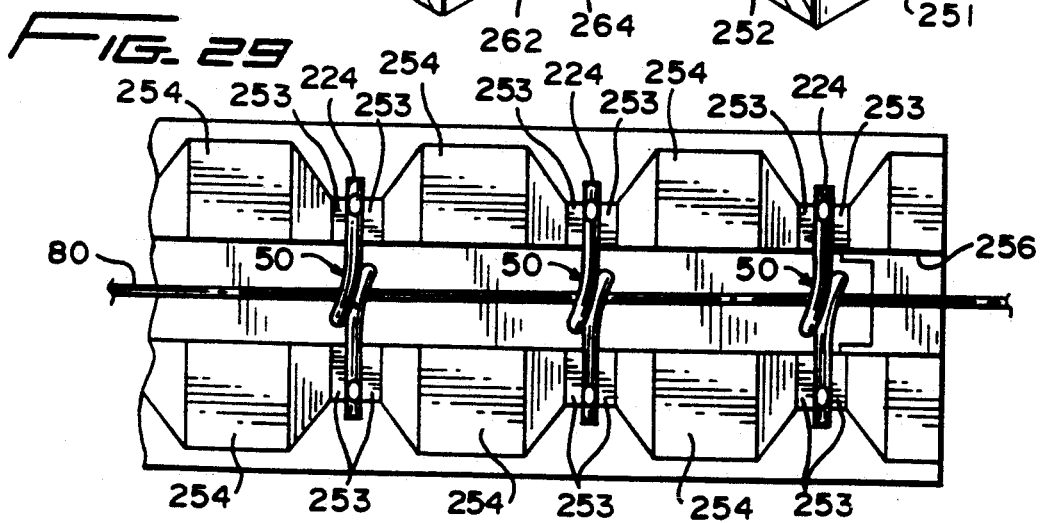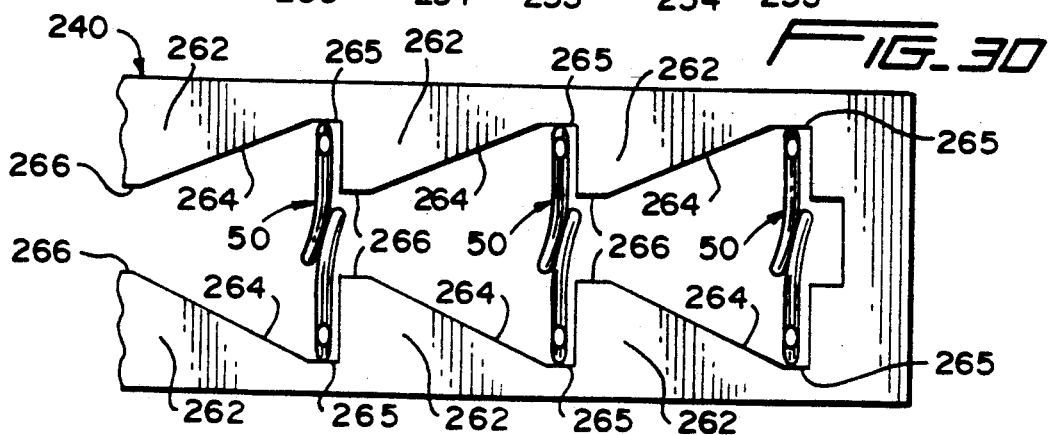

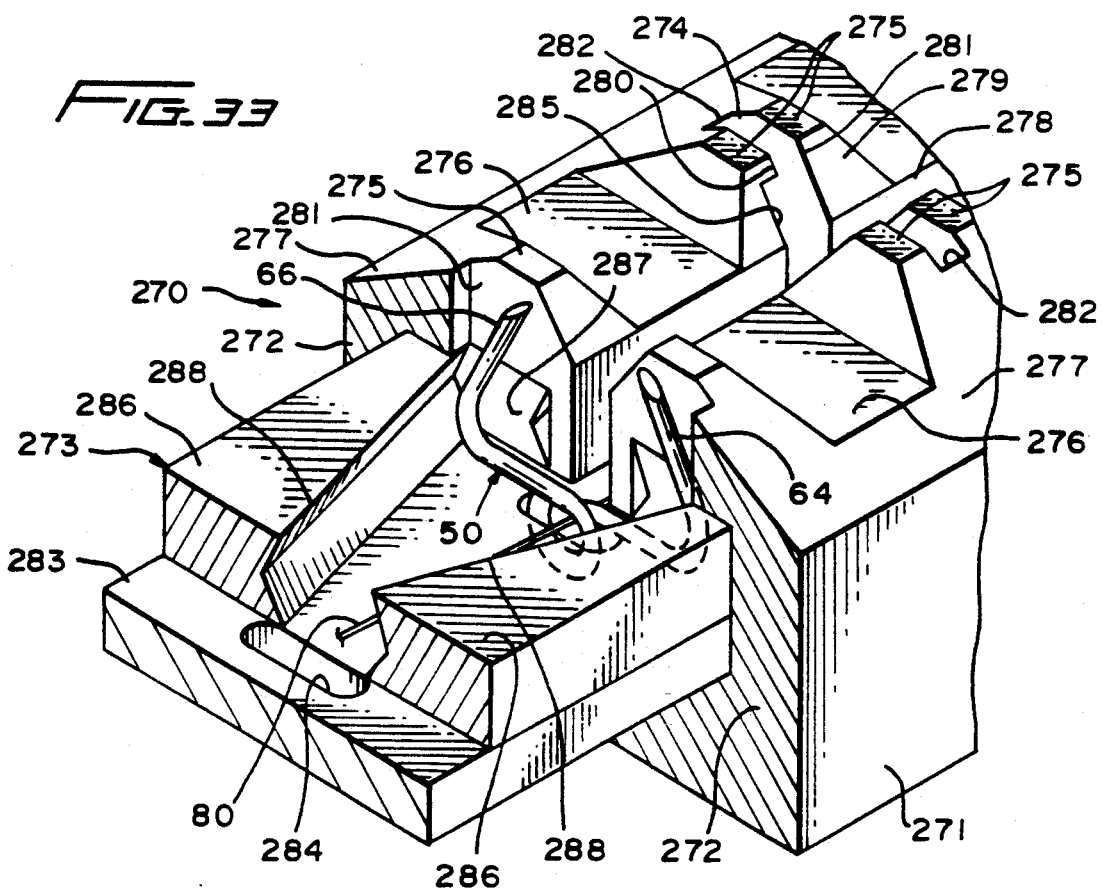
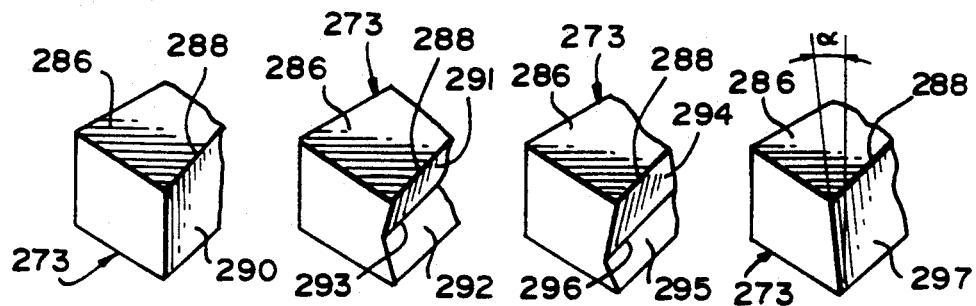
FIG.34A  FIG.34B  FIG.34C  FIG.34D
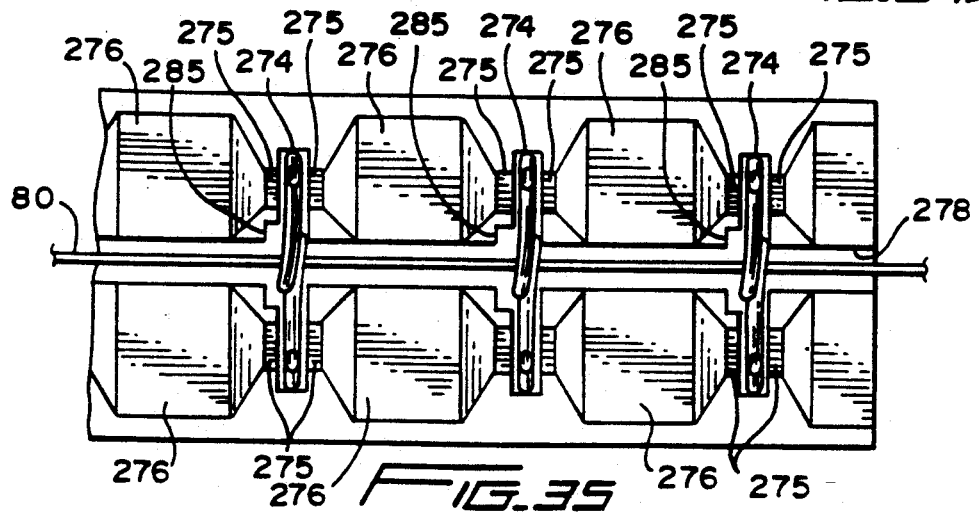
FIG.35

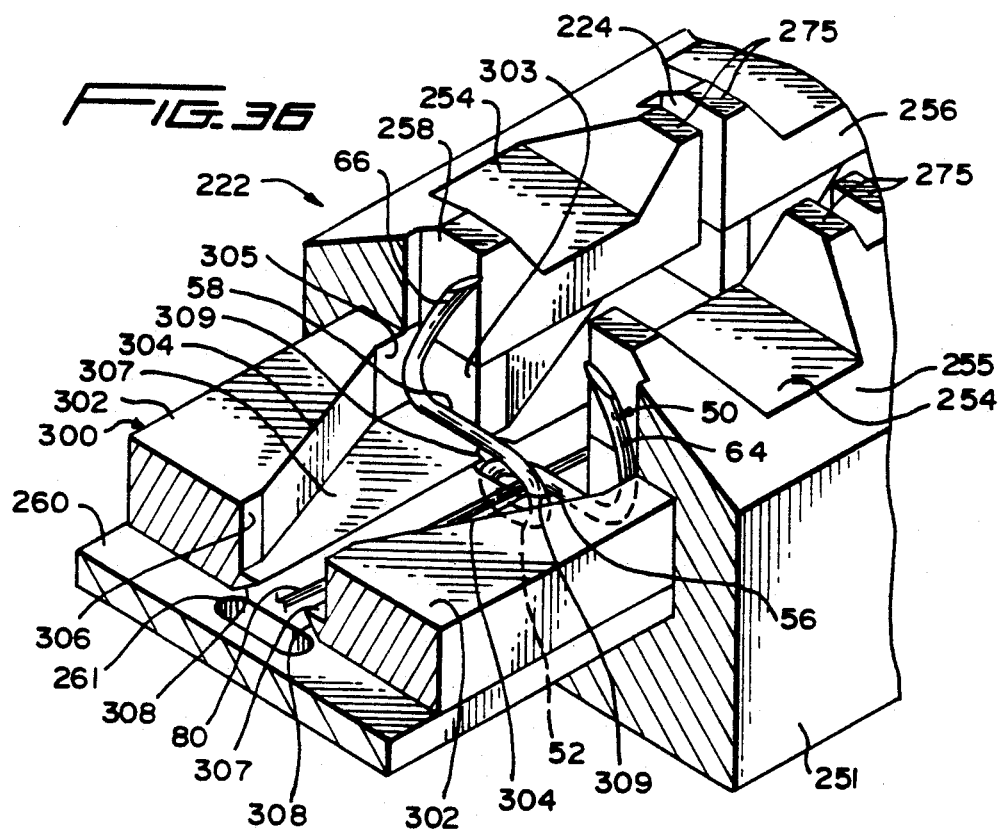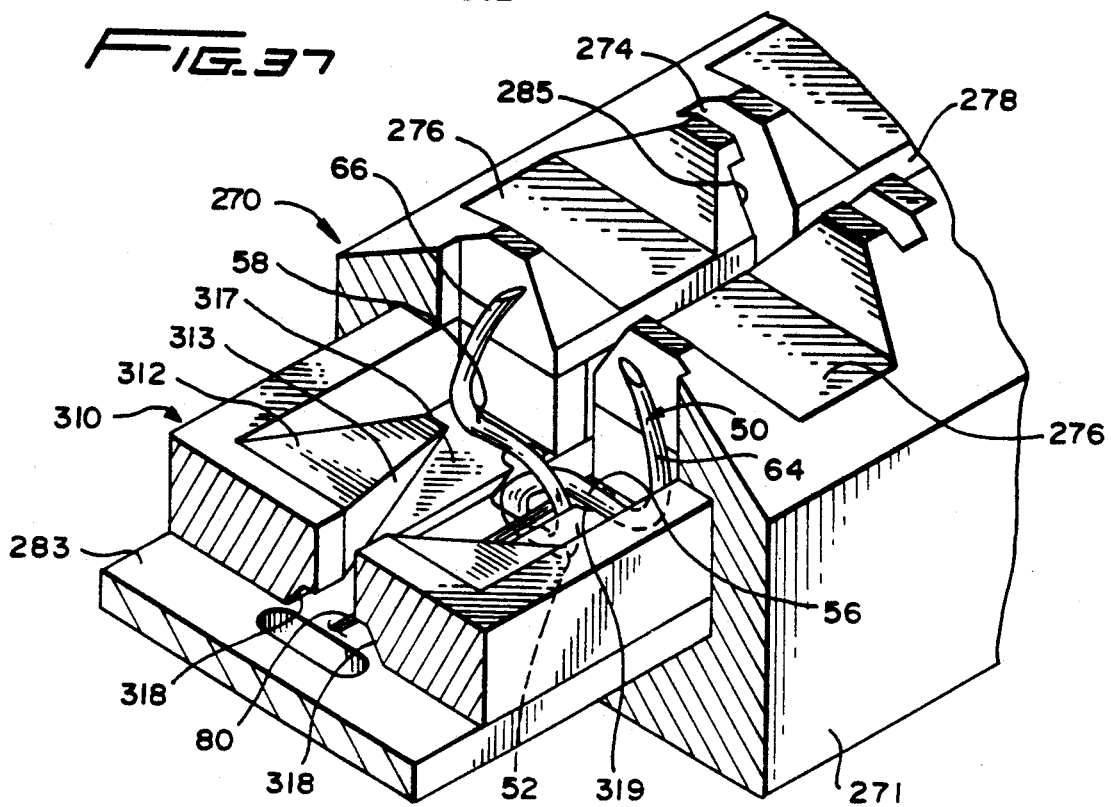

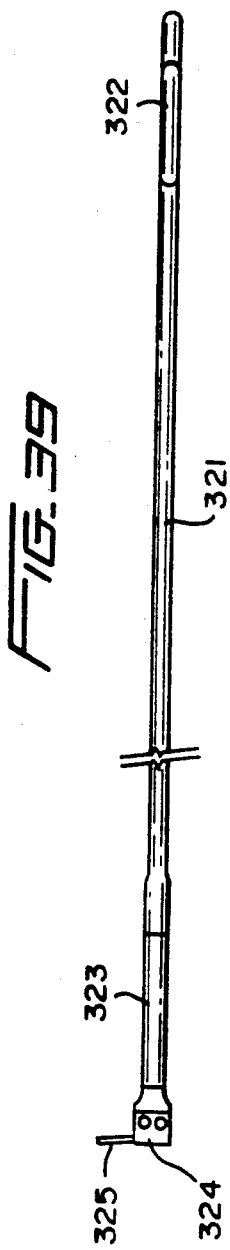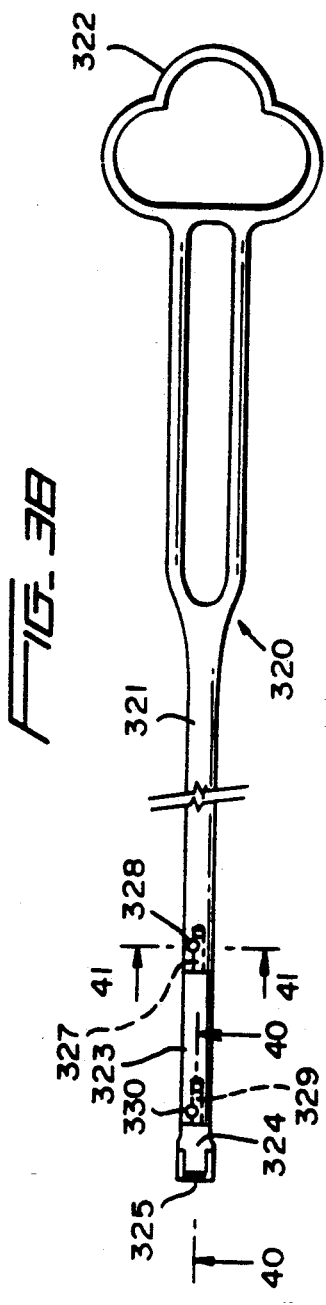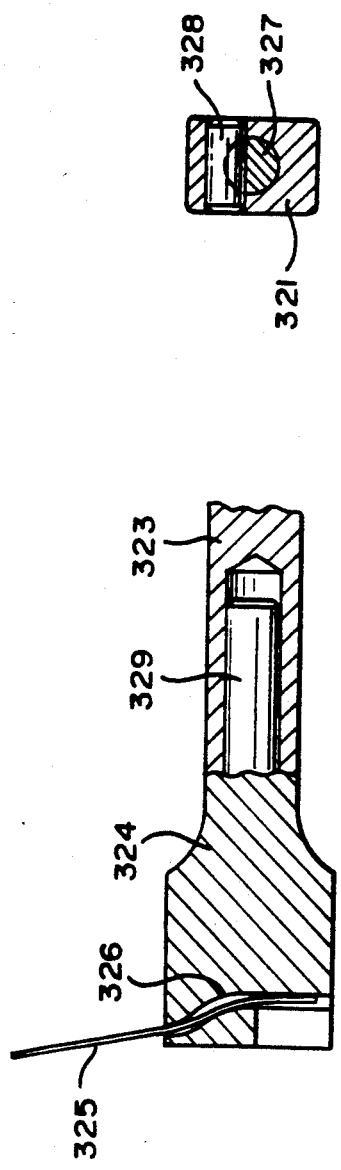

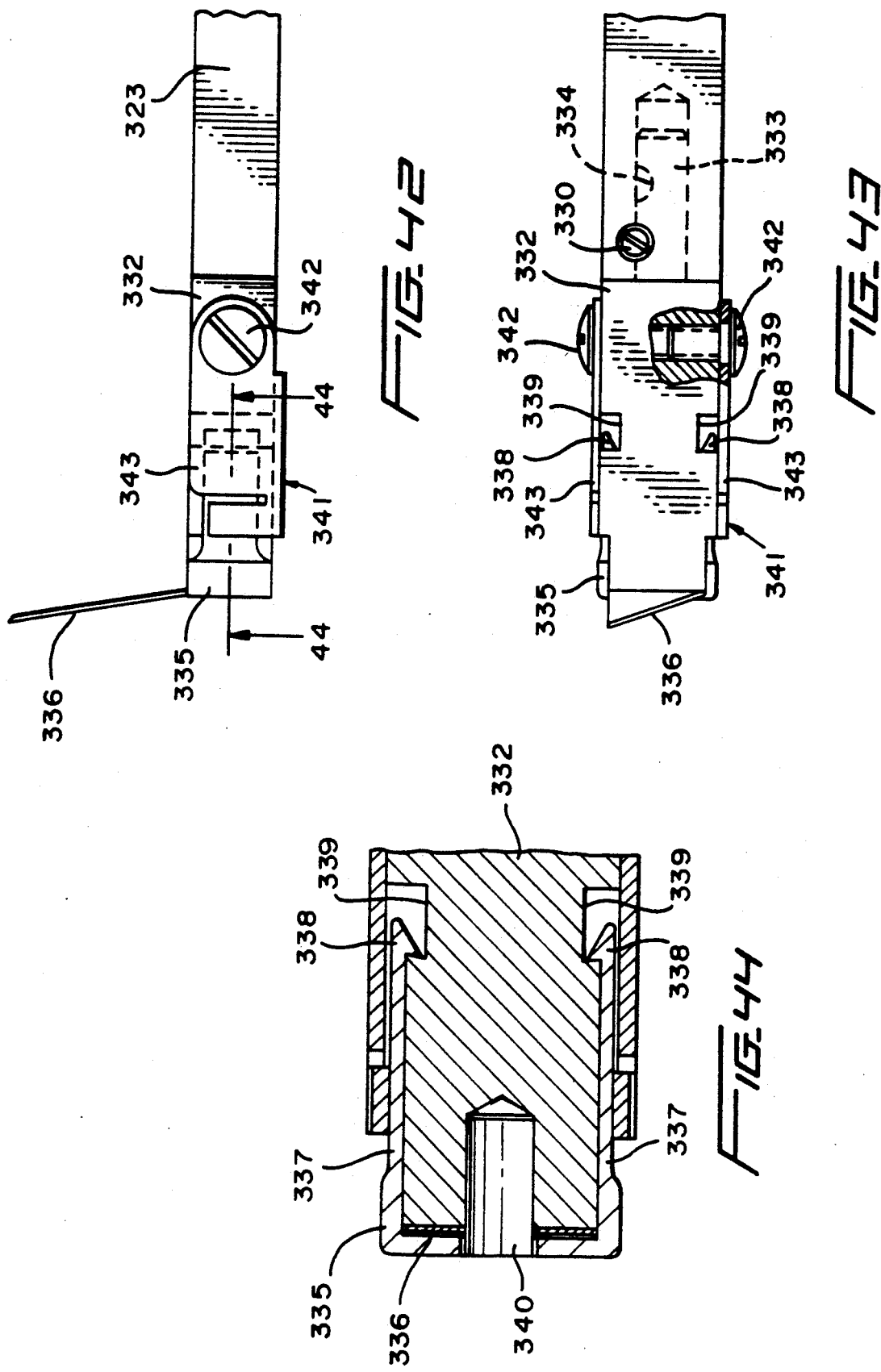

SURGICAL INSTRUMENT AND STAPLES FOR APPLYING PURSE STRING SUTURES

BACKGROUND OF THE INVENTION

1. Field of the Invention

The present invention generally relates to a surgical instrument and staples for applying purse string sutures to human tissue and, more particularly, to a surgical instrument and method in which a purse string suture is secured to human tissue by a plurality of staples. In addition, this invention relates to a surgical staple for securing a purse string suture to human tissue in which the staple body is adapted to be slidably attached to the purse string suture.

2. Description of the Prior Art

In the prior art, it is known to use a purse string suture to close a tubular section of tissue, e.g., intestinal tissue, prior to the performance of an end-to-end anastomosis with a circular suturing instrument. The purse string suture is attached to a surgical needle which is used by a surgeon to manually stitch the purse string suture about the periphery of the tubular section of tissue. After the purse string suture is stitched to the tissue, the ends of the purse string suture are pulled to tighten the stitches and draw the tissue together. Then, the purse string suture is wrapped and tightened about the tubular section of tissue. In the manual stitching of the purse string suture, it is difficult to obtain uniform penetration of the purse string suture into the tissue. It is also difficult to obtain stitches which are uniform in length and are evenly spaced apart. As a result, some of the stitches may rip away from the tissue when the ends of the purse string suture are pulled.

Purse string suture devices are known in the prior art which comprise a pair of serrated tissue clamping jaws provided with teeth for clamping the tissue to be sutured therebetween. Such devices include needle passages which extend through the teeth on each jaw for receiving a needle attached to a suture to be threaded through the tissue. In use, the tissue to be sutured is clamped between the jaws and the needle is manually passed through the needle passages in both jaws to thread the suture through the tissue. Thereafter, the jaws are opened and the purse string suture is tightened and wrapped to draw the tissue together. Because the tissue may be gathered unevenly between the jaws, it is sometimes difficult to obtain uniform penetration of the needle and suture into the tissue. Thus, when the ends of the purse string suture are pulled to gather the tissue together, there is a tendency for at least some of the stitches formed by the purse string suture to rip away from the tissue. Also, it is possible that some of the stitches may extend through both walls of the tubular section of tissue with the result that the tissue is not uniformly drawn together when the ends of the purse string suture are pulled to draw the tissue together.

In the prior art, it has been proposed to provide purse string suture devices which utilize a plurality of staples for applying purse string sutures to human tissue. Both anvil carrying devices and anvilless devices have been proposed for applying the staples and the purse string sutures to the tissue.

For example, U.S. Pat. No. 4,749,114 discloses a purse string applicator which includes an anvil carrier with a plurality of anvils for insertion in a tubular section of tissue and a pair of staple cartridges disposed on opposite sides of the anvil carrier. Each cartridge has a row of staples and the purse string suture extends across each row of staples. The applicator includes a pair of pushers each having a plurality of pusher fingers for driving the staples from the cartridges through the tissue against the anvils of the carrier. The staples in each row are deformed and secured to the tissue and the purse string suture is slidably retained between the staples and the tissue.

In addition, U.S. Pat. No. 4,821,939 discloses an anvilless surgical stapler for applying purse string sutures to human tissue. The stapler includes a pair of staple cartridges each having a plurality of openings for receiving a plurality of surgical staples. The cartridges include opposed projections which define grooves at both ends of the cartridges to receive a purse string suture. Each cartridge includes a pair of staple forming lips which define an outlet of lesser width than the openings. Each cartridge includes a plurality of pushers for driving the staples from the openings through the outlets and into the tissue clamped between the cartridges. As the staples are expelled from the openings, the lips deform the staple legs inwardly toward each other to penetrate into and grip the tissue. The purse string suture is located underneath each staple and is thereby attached to the tissue.

In the above examples, the purse string suture is located underneath the staples and is retained against the tissue by the staples. Consequently, when the ends of the purse string suture are pulled by a surgeon to draw the tissue together, there is some resistance to movement of the purse string suture relative to the staples and tissue. Thus, it is possible that some portions of the tissue may not be tightly drawn together by pulling on the ends of the purse string suture.

Accordingly, it is desirable to provide a surgical staple for securing a purse string suture to human tissue which does not clamp the purse string suture against the tissue. Also, it is desirable to provide a surgical staple for securing a purse string suture which presents minimal resistance to the movement of the purse string suture after the staple is secured to the tissue. In addition, it is desirable to provide a surgical staple for securing a purse string suture in which the staple body is slidably attached to the purse string suture.

Further, it is desirable to provide a method for securing a purse string suture to human tissue by a plurality of staples which are slidably attached to the purse string suture and present minimal resistance to the movement of the purse string suture relative to the tissue. Also, it is staple cartridge in which the purse string suture can be slidably attached to the surgical staples prior to the operation of the instrument to secure the staples and the purse string suture to the tissue.

SUMMARY OF THE INVENTION

The present invention achieves an improved surgical staple for securing a purse string suture to human tissue. The surgical staple comprises a staple body comprising an elongated strip of deformable material including a pair of legs adapted to be inserted into the tissue, the legs being deformable upon insertion into the tissue to secure the staple body to the tissue, and the staple body including means for slidably attaching the purse string suture to the staple. Preferably, the receiving means comprises an eyelet formed on the staple body through which the purse string suture is threaded. The eyelet can be located on the opposite side of the staple body from the staple legs or on the same side of the staple body as the staple legs.

In a preferred embodiment of the surgical staple, the staple body is formed into a loop to provide an eyelet through which the suture is threaded. The loop is formed on the opposite side of the staple body from the staple legs or on the same side of the staple body as the staple legs.

Another embodiment of the surgical staple comprises a staple body including two or more legs adapted to be inserted into the tissue, the legs including barbed ends for anchoring the legs to the tissue, and the staple body including means for slidably receiving the purse string suture. Preferably, the surgical staple comprises a staple body shaped into a ring to provide an eyelet for receiving a purse string suture and including two or more legs with barbed ends for anchoring the legs to the tissue. In a preferred embodiment of the surgical staple, a plurality of legs extend in a fan-like configuration from the staple body. The legs are bent alternately forward and rearward relative to the ring.

Another aspect of the invention relates to an improved method for securing a purse string suture to a tubular section of tissue. The method comprises the steps of positioning a plurality of staples about the periphery of a tubular section of tissue, slidably attaching a purse string suture to the staples, and driving the staples into the tissue to secure the purse string suture thereto. Preferably, each of the staples includes an eyelet through which the purse string suture is threaded to attach the purse string suture to the staples.

The present invention also achieves an improved surgical instrument for applying purse string sutures to human tissue. The purse string suture instrument comprises a pair of staple cartridges having opposed tissue clamping surfaces for clamping the tissue therebetween. A row of staple receiving slots is formed in each of the cartridges with each slot being adapted to receive a staple with its legs pointing toward the tissue clamping surface of the cartridge. A central slot extends along the tissue clamping surface of each cartridge for receiving a purse string suture connected to the staples in each of the staple receiving slots. A staple pusher bar is slidably mounted in each cartridge and adapted to engage and bend the legs of each staple toward the tissue clamping surface of the cartridge upon movement of the staple pusher bar relative to the cartridge. Actuating means is provided for sliding the pusher bar in each staple cartridge to bend the staple legs and secure the staples and the purse string suture to the tissue clamped between the cartridges.

Preferably, the central slot in each staple cartridge intersects each of the staple receiving slots therein. Also, the staple pusher bar is movable relative to the cartridge in a direction parallel to the row of staples therein. The pusher bar includes a series of opposed pairs of wedge-shaped protrusions corresponding to the staple receiving slots in the cartridge, with each pair of wedge-shaped protrusions being adapted to engage and bend the legs of the staple toward the tissue clamping surface into an overlapped configuration when the staple pusher bar is moved longitudinally relative to the cartridge.

According to another aspect of the invention, a staple cartridge comprises an elongated housing including a tissue engaging surface, a plurality of transverse slots extending into the housing from the tissue engaging surface for receiving staples therein, and an elongated central slot for receiving a purse string suture attached to each of the staples. The elongated central slot extends longitudinally along the housing and intersects the transverse slots. A staple pusher bar is slidably mounted for longitudinal movement in the housing with the staple pusher bar being adapted to engage and bend the legs of each staple toward the tissue clamping surface to secure the staples and the purse string suture to the tissue.

BRIEF DESCRIPTION OF THE DRAWINGS

The foregoing and other objects, aspects and advantages will be better understood from the following detailed description of the preferred embodiments of the invention with reference to the drawings, in which:

FIG. 11 is an enlarged view of a modified form of the surgical staple shown in FIG. 1;

FIG. 12 is an enlarged view of another form of the surgical staple shown in FIG. 1;

FIG. 13 is an enlarged view of a modified form of the surgical staple shown in FIG. 4;

FIG. 14 shows a purse string suture secured to a tubular section of tissue by a plurality of staples in accordance with this invention;

FIG. 15 shows a fifth embodiment of a surgical staple for securing a purse string suture to human tissue which includes a plurality of legs provided with barbed ends for anchoring the staple in the tissue;

FIG. 16 is an end view of the surgical staple of FIG. 15;

FIG. 17 shows the surgical staple of FIG. 15 anchored in the tissue with a purse string suture threaded therethrough;

FIG. 18 shows a purse string suture threaded into a plurality of surgical staples of the type shown in FIG. 1;

FIG. 19 shows a purse string suture threaded into a plurality of surgical staples of the type shown in FIG. 4;

FIG. 20 shows a purse string suture threaded into a plurality of surgical staples of the type shown in FIG. 15;

FIG. 21 is a perspective view showing the purse string instrument of the present invention with its jaws open;

FIG. 22 is a side view of the purse string suture instrument with its jaws closed;

FIG. 23 is a bottom view of the purse string suture instrument;

FIG. 24 is an end view of the purse string string suture instrument;

FIG. 25 is a partially cutaway plan view of the opposite side of the purse string suture instrument shown in FIG. 22;

FIG. 26 is an enlarged section taken along line 26—26 of FIG. 22;

FIG. 27 is a partially cutaway view of one of the jaws of the instrument;

FIG. 28 is a partially cutaway perspective view of a first embodiment of a staple cartridge for use with the purse string suture instrument;

FIG. 29 is a top view of the tissue clamping surface of the staple cartridge of FIG. 28;

FIG. 30 is a top view of the staple pusher bar used in the staple cartridge of FIG. 28;

FIG. 33 is a partially cutaway perspective view of a second embodiment of a staple cartridge for use with the purse string suture instrument;

FIGS. 34A-D illustrate modifications of the staple pusher bar of the cartridge of FIG. 33;

FIG. 35 is a top view of the tissue clamping surface of the staple cartridge of FIG. 33;

FIG. 36 is a partially cutaway perspective view of a third embodiment of a staple cartridge for use with the staple shown in FIG. 19;

FIG. 37 is a partially cutaway perspective view of a fourth embodiment of a staple cartridge for use with the staple shown in FIG. 19;

FIG. 38 is a side view of a tissue cutting tool used with the purse string instrument of the present invention;

FIG. 39 is a plan view of the tissue cutting tool of FIG. 38;

FIG. 40 is an enlarged section taken along line 40—40 of FIG. 38;

FIG. 41 is an enlarged section taken along line 41—41 of FIG. 38;

FIG. 42 is an enlarged, partially cutaway plan view of another embodiment of the tissue cutting tool;

FIG. 43 is a side view of the tissue cutting tool of FIG. 42; and

FIG. 44 is an enlarged section taken along line 44—44 of FIG. 42.

DETAILED DESCRIPTION OF PREFERRED EMBODIMENTS

Figure 1:
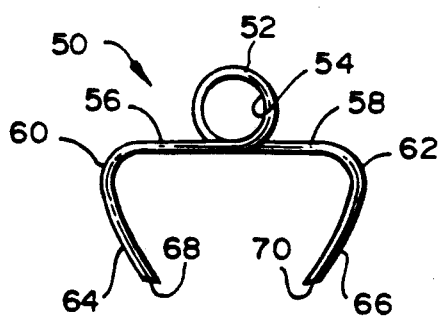
FIG. 1 is a side view of a first embodiment of a surgical staple for securing a purse string suture to human tissue.
Figure 2:
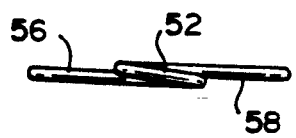
FIG. 2 is a top view of the surgical staple of FIG. 1.

Referring to FIG. 1, the present invention is embodied in a surgical staple, generally 50, for securing a purse string suture to human tissue. The staple 50 has a staple body comprising an elongated strip of deformable material which is shaped into a loop 52 at the center of the strip. The loop 52 provides an opening or eyelet 54 for receiving a purse string suture. The staple body also has a pair of arms 56 and 58 which extend substantially horizontally from opposite sides of the loop 52. The arms 56 and 58 have outer portions 60 and 62, respectively, which curve downwardly and provide a pair of depending legs 64 and 66 which are angled inwardly toward each other. The tips 68 and 70 of the legs 64 and 66 are bevelled to provide sharp points which facilitate the insertion of the legs 64 and 66 into human tissue. The loop 52 is formed on the opposite side of the staple body from legs 64 and 66.

Figure 3:
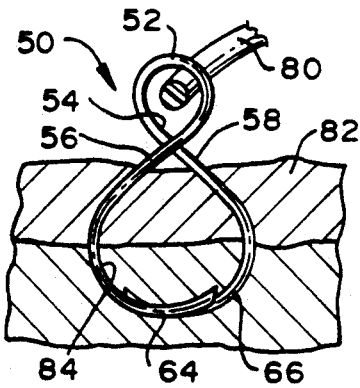
FIG. 3 shows the surgical staple of FIG. with its legs deformed to attach the staple and a purse string suture to the tissue.

As shown in FIG. 3, the surgical staple 50 is particularly useful for securing a purse string suture 80 to a section of human tissue 82, e.g., a tubular section of intestinal tissue. The purse string suture 80 is threaded through the eyelet 54 defined by the loop 52 and is slidably attached to the staple 50. The arms 56 and 58 are deformed by applying pressure to the outer portions 60 and 62-(FIG. 1) to insert the legs 64 and 66 into the tissue 82. When the deformation is completed, the legs 64 and 66 are moved into an overlapping configuration (FIG. 3). Thus, the staple 50 is formed into the configuration of a figure eight including the small upper loop 52 for insertion of the purse string suture 80 and a large lower loop 84 defined by arms 56 and 58 and overlapping legs 64 and 66 for connection to the tissue 82.

Figure 4:
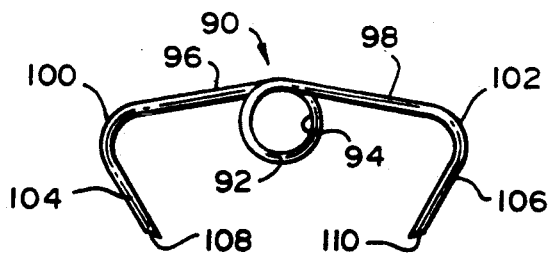
FIG. 4 is a side view of a second embodiment of a surgical staple for securing a purse string suture to human tissue.

Referring to FIG. 4, in a second embodiment of the invention, a surgical staple, generally 90, includes a staple body comprising an elongated strip of deformable material which is shaped into a loop 92 at the center of the strip. The loop 92 provides an opening or eyelet 94 for receiving a purse string suture. The staple body also has a pair of arms 96 and 98 which extend from opposite sides of the loop 92 and which slope slightly downward from the horizontal. The outer portions 100 and 102 of arms 96 and 98 are curved downwardly and provide a pair of legs 104 and 106 which are angled inwardly toward each other. The tips 108 and 110 of legs 104 and 106 are bevelled to provide sharp points which facilitate the insertion of legs 104 and 106 into the tissue. The loop 92 is formed on the same side of the staple body as the legs 104 and 106.

Figure 6:
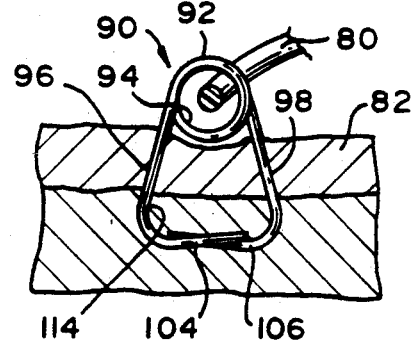
FIG. 6 shows the surgical staple of FIG. 4 with its legs deformed to attach the staple and a purse string suture to the tissue.

As shown in FIG. 6, the surgical staple 90 is used to secure the purse string suture 80 to the human tissue 82. The purse string suture 80 is inserted into the eyelet 94 defined by the loop 92 and is slidably attached to the staple 90. The arms 96 and 98 are deformed by applying pressure to the outer portions 100 and 102 (FIG. 4) to insert the legs 104 and 106 into the tissue 82. When the deformation is completed, the legs 104 and 106 are moved into an overlapping configuration (FIG. 6). As a result, the staple 90 is deformed into a double-loop configuration with the small upper loop 92 for insertion of the purse string suture 80 which is enclosed by a large lower loop 114 defined by the arms 96 and 98 and legs 104 and 106 for connection to the tissue 82.

Figure 7:
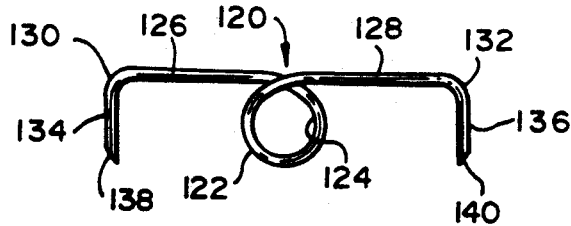
FIG. 7 is a side view of a third embodiment of a surgical staple for securing a purse string suture to human tissue.

Referring to FIG. 7, in a third embodiment of the invention, a surgical staple, generally 120, includes a staple body comprising an elongated strip of deformable material which is shaped into a loop 122 at the center of the strip. The loop 122 provides an opening or eyelet 124 for receiving a purse string suture. The staple body also has a pair of arms 126 and 128 which extend substantially horizontally from opposite sides of the loop 122. The outer portions 130 and 132 of arms 126 and 128 curve downwardly and provide a pair of depending legs 134 and 136 extending perpendicularly downward from arms 126 and 128, respectively. The tips 138 and 140 of the legs 134 and 136 are bevelled to provide sharp points which facilitate the insertion of the legs 134 and 136 into human tissue. The loop 122 is formed on the same side of the staple body as the legs 134 and 136.

Figure 8:
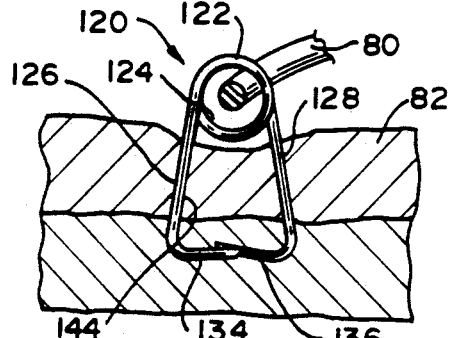
FIG. 8 shows the surgical staple of FIG. 7 with its legs deformed to attach the staple and a purse string suture to the tissue.
Figure 5:
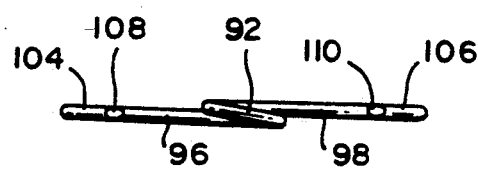
FIG. 5 is a bottom view of the surgical staple of FIG. 4.

As shown in FIG. 8, the surgical staple 120 is used to secure the purse string suture 80 to the human tissue 82. The purse string 80 is inserted into the eyelet 124 defined by the loop 122 and is slidably attached to the staple 120. The arms 126 and 128 are deformed by applying pressure to the outer portions 130 and 132 (FIG. 5) to insert the legs 126 and 128 into the tissue 82. When the deformation is completed, the legs 134 and 136 are moved into an overlapping configuration (FIG. 8). As a result, the staple 120 is deformed into a double-loop configuration with a small upper loop 122 for insertion of the purse string suture 80 which is enclosed by a large lower loop 144 for connection to the tissue 82.

Figure 9:
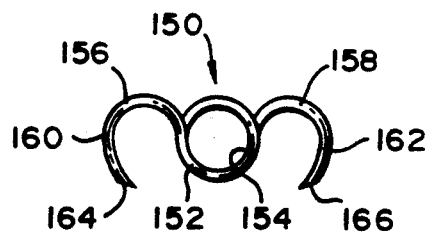
FIG. 9 is a side view of a fourth embodiment of a surgical staple for securing a purse string suture to human tissue.

Referring to FIG. 9, in a fourth embodiment of the invention, a surgical staple, generally 150, includes a staple body comprising an elongated strip of deformable material which is shaped into a loop 152 at the center of the strip. The loop 152 provides an opening or eyelet 154 for receiving a purse string suture. The staple body also has a pair of arms 156 and 158 extending from opposite sides of the loop 152 which are each curved in a semi-circular configuration. The arms 156 and 158 terminate in a pair of depending legs 160 and 162, respectively, which point downwardly from the staple body and toward each other. The tips 164 and 166 of legs 160 and 162 are bevelled to provide sharp points to facilitate the insertion of the legs 160 and 162 into the tissue.

Figure 10:
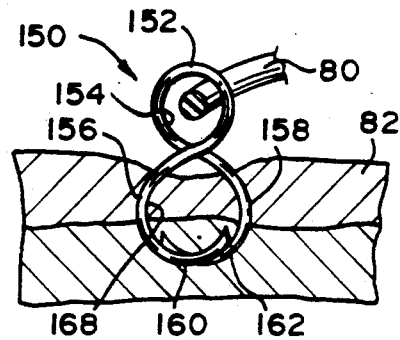
FIG. 10 shows the surgical staple of FIG. 9 with its legs deformed to attach the staple and a purse string suture to the tissue.

As shown in FIG. 10, the surgical staple 150 is used to secure the purse string suture 80 to the human tissue 82. The purse string suture 80 is inserted into the eyelet 154 defined by the loop 152 and is slidably attached to the staple 150. The arms 156 and 158 are deformed by applying pressure to the outer portions thereof to insert the legs 160 and 162 into the tissue 82. When the deformation is completed, the legs 160 and 162 are moved into an overlapping configuration (FIG. 10). Thus, the staple 150 tends to assume the configuration of a figure eight including the small upper loop 152 for insertion of the purse string suture 80 and a large lower loop 168 defined by arms 156 and 158 and overlapping legs 160 and 162 for connection to the tissue 82.

In the embodiments of FIGS. 1, 4, 7 and 9, the body of the surgical staple 50 comprises an elongated strip of deformable material such as stainless steel. Preferably, the strip has a round cross section with a diameter in the range of 0.3 to 0.5 millimeters.

Referring to FIG. 11, in a modified form of the first embodiment, the outer portions 60 and 62 of arms 56 and 58 are curved in a semi-circular shape to provide the legs 64 and 66. The staple 50 consists of an elongated strip of stainless steel having a round cross section with a diameter of 0.3 mm. The loop 52 is round and its inner diameter, i.e., the diameter of eyelet 54 is 0.7 mm. The staple 50 has a width of 5 mm, a height (without the loop 52) of 2.5 mm, and an overall height (including the loop 52) of 3.5 mm.

Referring to FIG. 12, in another form of the first embodiment, staple 50 includes a loop 52 which is generally triangular in shape. The width of eyelet 54 is 1 mm. The staple 50 consists of an elongated strip of stainless steel having a round cross section with a diameter of 0.3 mm. The staple 50 has a width of 5 mm, a height (without the loop 52) of 2.5 mm, and an overall height (including the loop 52) of 3.5 mm.

Referring to FIG. 13, in an example of the second embodiment, the staple 90 consists of an elongated strip of stainless steel having a round cross section with a diameter of 0.3 mm. The diameter of eyelet 94 defined by loop 92 is 0.8 mm. The staple 90 has an overall width of 5 mm and an overall height of 2.5 mm.

Referring to FIG. 15, in a fifth embodiment of the invention, a surgical staple, generally 170, comprises a staple body in the form of a ring 172 which provides a circular eyelet 174 for receiving a purse string suture. The staple body includes a plurality of legs 176 extending downward in a fan-like configuration from the ring 172. Each leg 176 includes a barb 178 formed adjacent to its lower end for anchoring the leg in human tissue.

As shown in FIGS. 15 and 16, the centermost leg 176 is located in the same vertical plane as ring 172. The other legs 176 are bent alternately forward and rearward relative to the ring 172 and the centermost leg 176. The barbs 178 on the bent legs 176 face outwardly away from the vertical plane of the ring 172.

As shown in FIG. 17, the surgical staple 170 is used to secure the purse string suture 80 to the human tissue 82. The purse string suture 80 is inserted into the eyelet 174 defined by the loop 172 and is slidably attached to the staple 170. Then, the surgical staple 170 is driven into the tissue 82 so that the legs 176 are driven below the surface of the tissue 82 while the ring 172 remains above the surface of the tissue 82. The barbs 178 anchor the legs 176 in the tissue with the ring 172 holding the purse string suture 80 at the surface of the tissue 82.

Referring to FIG. 14, in the method of the present invention, a plurality of surgical staples of the type disclosed herein are used to secure the purse string suture 80 to a tubular section of tissue 82. Although a plurality of staples 50 is shown, it is understood that any of the above staple embodiments can be used.

In accordance with the method, a plurality of staples 50 are positioned about the periphery of the tubular section of tissue 82. The purse string suture 80 is attached to the staples by threading the purse string suture 80 through the eyelets 54 provided in the staples 50. Then, the staples 50 are driven into the tissue 82 to secure the purse string 80 thereto.

After the purse string suture 80 is secured to the tubular section of tissue 82, the opposite ends of the purse string suture 80 are pulled to draw the tissue together. The eyelets 54 of the staples 50 slidably support the purse string suture above the tissue 82 so that the staples 50 offer minimal resistance to movement of the purse string suture 80 when its ends are pulled. To complete the procedure, the purse string suture 80 is tightened and wrapped about the tubular section of tissue 82.

As shown in FIG. 18, a plurality of staples 50 of the type shown in FIG. 1 can be used to secure the purse string suture 80 to the tubular section of tissue 82. The purse string suture 80 is threaded through the loops 52 of the staples 50 and is slidably received therein. With the staples 50 positioned about the periphery of tubular section of tissue 82, the staples 50 are deformed to bend the staple legs 64 and 66 into an overlapping configuration (FIG. 3) to form the loop 84 extending into the tissue 82 to secure the purse string suture 80 thereto.

Similarly, as shown in FIG. 19, a plurality of staples 90 of the type shown in FIG. 4 can be used to secure the purse string suture 80 to the tubular section of tissue 82. The purse string suture 80 is threaded through the loops 92 of the staples 90 and is slidably received therein. With the staples 90 positioned about the periphery of the tubular section of tissue 82, the staples 90 are deformed to bend the staple legs 104 and 106 into an overlapping configuration (FIG. 6) to form the loop 114 extending into the tissue 82 to secure the purse string 80 thereto.

Further, as shown in FIG. 20, a plurality of staples 170 of the type shown in FIG. 15 can be used to secure the purse string suture 80 to the tubular section of tissue 82. The purse string suture 80 is threaded through the eyelets formed in the staples 170 and is slidably received therein. When the staples 170 are positioned about the periphery of the tubular section of tissue 82, the staples 170 are driven into the tissue 82 to secure the purse string suture thereto. The barbed ends of legs 176 anchor the staples 170 to the tissue.

Referring to FIGS. 21 and 22, the invention is embodied in a surgical stapling instrument 200 for applying purse string sutures to human tissue. The surgical instrument 200 comprises a pair of elongated handles 201 and 202 pivotally connected by a pivot pin 203 in a scissors-like arrangement. A pair of finger grips or rings 204 and 205 is provided at the rear of handles 201 and 202, respectively, to facilitate the handling and operation of the surgical instrument 200 by a surgeon. The handles 201 and 202 are provided with latch arms 206 and 207 which project inwardly from the finger grips 204 and 205, respectively. The latch arms 206 and 207 are adapted to interlock when the handles 201 and 202 are pivoted together to a closed position. A finger rest 208 projects rearwardly from the bottom of finger grip 204.

As shown in FIGS. 22 and 23, the handles 201 and 202 include front portions 209 and 210 which support a pair of tissue clamping jaws 211 and 212, respectively. Preferably, the jaws 211 and 212 project perpendicularly from the front handle portions 209 and 210. As shown in FIG. 24, the jaws 211 and 212 have flat, outer surfaces 213 and 214, respectively, which are tapered inwardly toward the outer tips of the jaws. Also, the jaws 211 and 212 have flat, inner surfaces 215 and 216, respectively, which are oriented at a slight angle with respect to each other. As a result, when the handles 201 and 202 are closed to bring the tips of jaws 211 and 212 together, the rear portions of the surfaces 215 and 216 are separated by a distance d which provides a small amount of play in the movement of handles 201 and 202 to bring the jaws 207 and 208 to a fully closed position.

As shown in FIGS. 21 and 22, the outer tip of jaw 211 includes a pair of tabs 217 which are received by side notches 218 formed at the tip of jaw 212. The tabs 217 maintain the jaws 211 and 212 in alignment when the handles 201 and 202 are closed. In addition, a flat tab 219 depends from the upper arm 209 at a point adjacent to the rear of the jaw 211. The depending tab 219 overlaps a flat surface 220 on the lower arm 210 when the handles 201 and 202 are closed.

As shown in FIG. 22, the jaws 211 and 212 support a pair of elongated staple cartridges 222 for receiving the surgical staples and the purse string sutures to be applied to the tissue. Each staple cartridge 222 includes a plurality of transverse slots 224 spaced uniformly apart along the cartridge 222 for receiving the staples to be attached to the tissue. Also, each of the staple cartridges 222 includes a staple forming mechanism, explained in more detail below, for driving the staples into the tissue clamped between the jaws 211 and 212 to attach the purse string suture to the tissue.

Referring to FIGS. 21 and 22, the purse string suture instrument 200 includes a staple actuating lever 225 pivotally mounted by a pivot pin 226 on the handle 201. The lever 225 is bifurcated at its front end to provide a slot 228 (FIG. 21) which allows the latch arm 206 to project upwardly through the lever 225. The latch arm 206 includes a rearwardly extending shoulder 228 which serves as a stop to limit the upward movement of the lever 225. An upright, bifurcated arm 229 is provided at the front of the lever 225 and is connected to an elongated flexible wire 230. As shown FIG. 25, the front end of wire 230 is formed into an elongated loop 232 which is slidably attached to the back of handle 201 by a screw 233. The front end of the loop 232 is attached to a pair of wires 234 which, in turn, are attached to a pair of pivot arms 236 for actuating the staple forming mechanisms of the cartridges 222 when the lever 225 is operated.

As shown in FIGS. 21 and 22, a locking disc 238 is pivotally mounted on a flange 239 which extends rearwardly from the finger grip 204. The locking disc 238 is pivotable between an upper position (FIG. 22) in which the lever 225 is engaged by the disc 238 and locked against the shoulder 228 and a lower position (FIG. 21) in which the disc 238 engages the finger rest 208 and the lever 225 is disengaged and unlocked for pivotal movement.

As shown in FIG. 27, the pivot arm 236 is pivotally mounted on the front handle portion 209 by a screw 242. The pivot arm 236 includes an upright finger 243 which is slidably received in a transverse slot 244 formed in a staple pusher bar 240 which is slidable longitudinally relative to the staple cartridge 222. The front end of the wire 234 is bent at a right angle and received in a slot 245 formed in the pivot arm 236. A curved spring 246 has its front end received in the slot 245 and its rear end anchored in a hole 247 formed in the front handle portion 209. The spring 246 includes a front portion 248 which curves in a clockwise direction around the screw 242 and a rear portion 249 which curves in a counterclockwise direction about a mounting screw 250. The spring 246 is arranged to normally bias the pivot arm 236 in a clockwise direction about the screw 242 so that the staple pusher bar 240 is biased into the staple cartridge 222. When the wire 234 is pulled rearwardly, the pivot arm 236 is pivoted in a counterclockwise direction against the bias of the spring 236 to slide the staple pusher bar 240 outward relative to the staple cartridge 222. As explained below, this sliding motion of the staple pusher bar 240 causes the staples to be deformed and secured to the tissue clamped between the jaws 211 and 212.

Referring to FIG. 28, a first embodiment of the staple cartridge 222 is adapted for use with the staple 50 (FIG. 1). The staple cartridge 222 comprises an elongated rectangular housing 251 including a pair of side walls 252 which slidably receive the staple pusher bar 240 therebetween. The staple cartridge 251 includes a plurality of transverse staple receiving slots 224 which extend vertically downward into the housing 251. As shown in FIG. 29, each staple receiving slot 224 is located between a pair of ridges 253 which extend upwardly from the top of the housing 251. Each pair of ridges 253 is separated by a valley or depression 254 from the next adjacent pair of ridges 253. The staple cartridge housing 251 is sloped upwardly and inwardly at its outer edges to define sloped surfaces 255 which terminate at the top of the ridges 253. An elongated vertical slot 256 extends longitudinally along the center of the housing 251. The tops of the ridges 253 provide flat tissue clamping surfaces.

The staple receiving slots 224 (FIG. 28) extend downwardly from the tissue clamping ridges 253 and intersect the central vertical slot 256. Each slot 224 is defined by a front wall 257, a rear wall 258 and a pair of end walls 259 which extend vertically downward into the housing 251. The staple 50 is inserted into the slot 254 with its legs 64 and 66 pointing upward toward the tissue clamping ridges 253. A plate 260 is secured inside the housing 251 beneath the pusher bar 240 and provides a ledge for supporting the arms 56 and 58 of the staple 50. The plate 260 includes a slot 261 aligned with each staple receiving slot 224 for receiving the loop 52 of the staple 50.

The staple pusher bar 240 (FIG. 30) consists of a generally rectangular plate provided with a series of opposed pairs of wedge-shaped protrusions 262 extending inwardly from its opposite sides. Each wedge-shaped protrusion 262 defines a flat upright surface 263 which is aligned with the rear wall 258 (FIG. 28) of the slot 224 and a staple forming edge 264 which is slanted inwardly toward the center of the pusher bar 240. The wedge-shaped protrusions 262 are oriented such that the clearance between the opposed staple forming edges 264 decreases as the pusher bar 240 is advanced in the direction of arrow A. Each opposed pair of staple forming edges 264 provides a first set of vertical surfaces 265 which are widely spaced apart and a second set of vertical surfaces 266 which are narrowly spaced apart. The staple 50 inserted in each slot 224 is located adjacent to the front wall 263 of the pusher bar 240. The purse string suture 80 is threaded through the loop 52 of the staple 50 in each slot 224.

Figure 31:
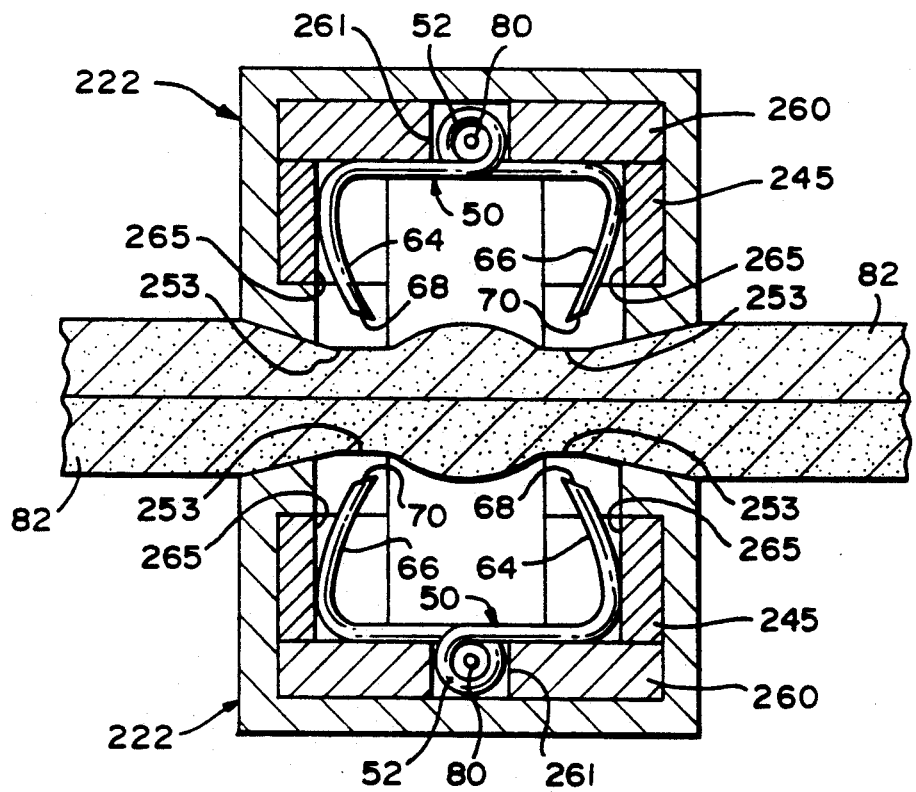
FIG. 31 is a vertical section showing the tissue clamped between a pair of staple cartridges prior to the operation of the staple pusher bars.
Figure 32:
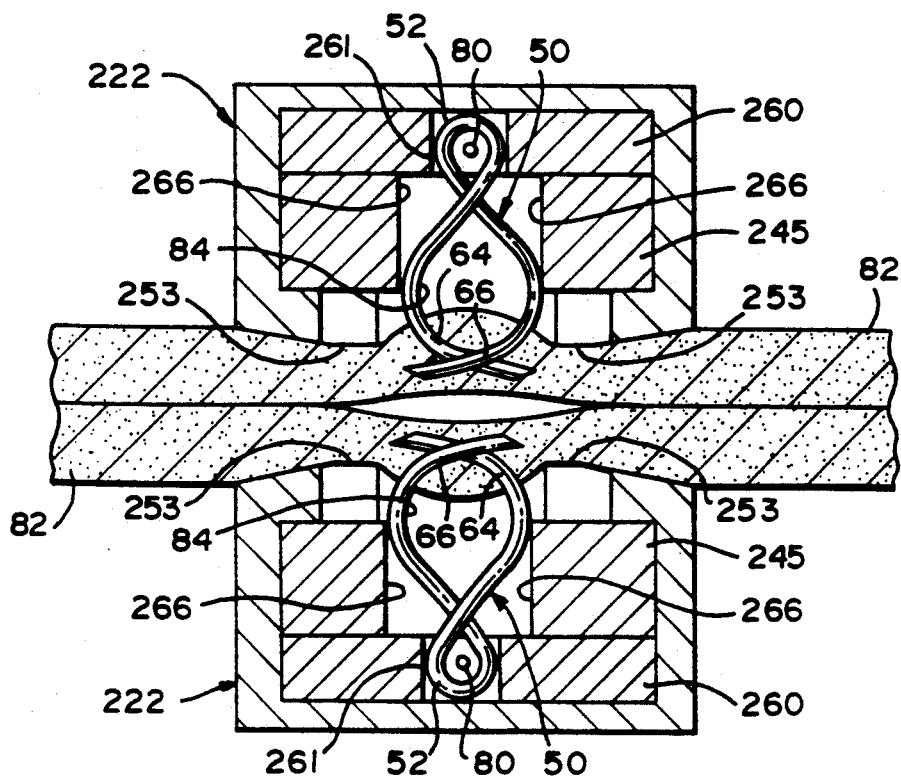
FIG. 32 is a vertical section showing the tissue clamped between a pair of staple cartridges after the operation of the staple pusher bars.

As shown in FIG. 31, the tissue 82 is clamped between the pair of staple cartridges 222 prior to the actuation of the staple pusher bars 240. The staple legs 64 and 66 are located between the surfaces 265 of the pusher bar 240. When the pusher bar 240 is advanced in the direction of arrow A (FIG. 30), the slanted edges 264 engage and bend the staple legs 64 and 66 toward each other. As shown in FIG. 32, the tips 68 and 70 of the staple legs 64 and 66 are guided into the tissue 82 between the ridges 253 of the staple cartridge 222. When the pusher bar 240 is fully advanced, the staple legs 64 and 66 are located between the surfaces 266 of the staple pusher bar 240. As a result, each staple 50 is deformed into the configuration of a figure eight with the staple legs 64 and 66 overlapped to form the loop 84 to secure the staple 50 and the purse string suture 80 to the tissue 82.

Referring to FIG. 33, in an alternative embodiment, a staple cartridge 270 comprises an elongated rectangular housing 271 including a pair of side walls 272 which slidably receive a staple pusher bar 273 therebetween. The staple cartridge 270 includes a plurality of transverse staple receiving slots 274 which extend vertically downward into the housing 271. Each staple receiving slot 274 is located between a pair of ridges 275 which extend upwardly from the top of the housing 271. Each pair of ridges 275 is separated by a valley or depression 276 from the next adjacent pair of ridges 275. The staple cartridge housing 271 is sloped upwardly and inwardly at its outer edges to define sloped surfaces 277 which terminate at the top of the ridges 275. An elongated vertical slot 278 extends longitudinally along the center of the housing 271. The top of the vertical slot 275 opens into a longitudinal V-shaped groove defined by inclined surfaces 279 which are sloped upwardly and outwardly from the vertical slot 278 and terminate at the top of ridges 275. The tops of the ridges 275 provide flat tissue clamping surfaces.

The staple receiving slots 274 extend downwardly from the tissue clamping ridges 275 and intersect the central vertical slot 278. Each slot 274 is defined by a front wall 280, a rear wall 281 and a pair of end walls 282 which extend vertically downward into the housing 271. The staple 50 is inserted into the slot 274 with its legs 64 and 66 pointing upward toward the tissue clamping ridges 275. A plate 283 is secured inside the housing 271 beneath the pusher bar 273 and provides a ledge for supporting the arms 56 and 58 of the staple 50. The plate 283 includes a notch 284 aligned with each staple receiving slot 274 for receiving the loop 52 of the staple 50.

Referring to FIGS. 33 and 35, in a preferred embodiment of the staple cartridge 270, each staple receiving slot 274 includes a recess 285 formed in its front wall 280. The purpose of the recess 285 is to enlarge the staple receiving slot 274 allow the legs 64 and 66 of the staple 50 to be bent into an overlapping configuration.

In the embodiment of FIG. 33, the staple pusher bar 273 includes a series of opposed pairs of wedge-shaped protrusions 286 extending inwardly from its opposite sides. Each wedge-shaped protrusion 286 defines a flat upright surface 287 aligned with the rear wall 281 of the slot 254. Also, each wedge-shaped protrusion 286 defines a staple forming edge 288 which is slanted inwardly toward the center of the pusher bar 273. In this embodiment, a V-shaped staple forming channel extends along the edge 288 of each wedge-shaped protrusion 286.

A staple 50 is inserted into each slot 274 with its legs 64 and 66 located adjacent to the front walls 281 of the pusher bar 273. The purse string suture 80 is threaded through the loop 52 of the staple 50 in each slot 274. When the pusher bar 273 is advanced in the direction of arrow A, the slanted edges 288 engage the staple legs 64 and 66 and bend the legs 64 and 66 toward each other. As a result, the tips 68 and 70 of the staple legs 64 and 66 are guided into the tissue 82 above the ridges 275 of the staple cartridge 270. When the pusher bar 273 is fully advanced, the staple 50 is deformed into the configuration of a figure eight with the staple legs 64 and 66 overlapped into the loop 84 (FIG. 3) to secure the staple 50 and the purse string suture 80 to the tissue 82.

FIGS. 34A–D illustrate examples of the configurations which can be used for the staple forming edge 288 of the staple pusher bar 273. In FIG. 34A, the protrusion 286 has a staple forming edge 288 consisting of an upright, vertically oriented surface 290. In FIG. 34B, the staple forming edge 288 includes sloped surfaces 291 and 292 which intersect at an elongated apex line 293 to define a V-shaped staple forming channel. The surfaces 291 and 292 are equal in size and are sloped at equal and opposite angles to the vertical. In FIG. 34C, the staple forming edge 288 has a V-shaped channel consisting of sloped surfaces 294 and 295 which are sloped at different angles and intersect at an elongated apex line 296 closer to the bottom of the staple pusher bar 273. In FIG. 34D, the staple forming edge 288 consists of a flat surface 297 which is sloped upwardly and outwardly at an angle α of approximately 10° from the vertical.

As shown in FIG. 36, another embodiment of the staple cartridge 222 includes a modified staple pusher bar 300 for use with a staple 50 (FIG. 19) in which the loop 52 is triangular in shape. The staple pusher bar 300 includes a series of opposed pairs of wedge-shaped protrusions 302 extending inwardly from its opposite sides. Each wedge-shaped protrusion 302 defines a flat upright surface 303 which is aligned with the rear wall 258 of the slot 224 and a staple forming edge 304 which is slanted toward the center of the pusher bar 301. The staple forming edges 304 provide a first set of vertical surfaces 305 which are widely spaced apart and a second set of vertical surfaces 306 which are narrowly spaced apart. On each side of the staple pusher bar 301, a ledge 307 projects inwardly toward the center of the pusher bar 301. Each ledge 307 is provided with an elongated bevelled edge 308 which allows the ledge 307 to move past the triangularly shaped loop 52 of the staple 50 when the staple pusher bar 300 is actuated. A pair of opposed notches 309 is formed in the ledges 307 to receive the arms 56 and 58 of the staple 50.

A shown in FIG. 37, another embodiment of the staple cartridge 270 includes a modified staple pusher bar 310 for use with a staple 50 (FIG. 19) in which the loop 52 is triangular in shape. The staple pusher bar 310 includes a plurality of pairs of wedge-shaped ramps each including an upwardly inclined surface 312 and an inwardly slanted surface 313 for deforming the legs 64 and 66 of the staple 50 when the pusher bar 310 is actuated. On each side of the staple pusher bar 310, a ledge 317 projects inwardly toward the center of the pusher bar 310. Each ledge 317 is provided with an elongated bevelled edge 318 which allows the ledge 317 to move past the triangularly shaped loop 52 of the staple 50 when the staple pusher bar 310 is actuated. A pair of opposed notches 319 is formed in the ledges 317 to receive the arms 56 and 58 of each staple 50.

Referring to FIG. 38, a tissue cutting tool or knife 320 includes an elongated handle 321 provided with a finger loop 322 at one end of the handle 321 to facilitate use of the knife 320 by a surgeon. The other end of handle 321 is attached to an extension rod 323 which, in turn, is attached to a knife head 324 which supports a cutting blade 325. The knife head 324 includes the curved slot 326 (FIG. 40) which extends across a front portion of the head 324. The cutting blade 325 is force fit into the slot 326 and projects outwardly and forwardly from one side of the head 324. The extension rod 323 includes an axially extending shaft 327 (FIG. 38) which is received in an axial bore formed in the handle 321. The shaft 327 is secured to the handle 321 by a transverse retainer screw 328. The knife head 324 includes an axially extending shaft 329 received in an axial bore formed in the extension rod 323 and secured by a retainer screw 330 to the extension rod 323. As shown in FIG. 41, the shaft 327 is notched to receive the retainer screw 328. Also, the shaft 329 is notched to receive the retainer screw 330.

Referring to FIG. 42, in an alternative embodiment to the tissue cutting tool, a knife head 332 which is detachably connected to the extension rod 323. The knife head 332 includes an axially extending shaft 333 (FIG. 43) which is received in an axial bore formed in the extension rod 323 and is secured by the retainer screw 330. The shaft 333 includes one or more notches 334 for receiving the retainer screw 330. The knife head 332 includes a removable support 335 which supports a knife blade 336 extending outwardly and forwardly from one side of the knife head 332. The knife support 335 includes a pair of flexible arms 337 provided with hooked ends 338 which are captured by a pair of notches 339 formed in the knife head 332. Also, a screw 340 (FIG. 44) is threaded into an axial bore 340 in the knife head 332 to secure the knife support 335 and the knife blade 336 to the knife head 332. A protective bracket 341 (FIG. 42) is pivotally attached to the knife head 332 by a pair of screws 342. The bracket 341 includes a pair of flanges 343 which normally cover the notches 339 when the knife support 335 is attached to the knife head 332.

To allow replacement of the knife support 335 and knife blade 336, the screws 342 are loosened and the bracket 341 is pivoted away from the knife head 332 to expose the notches 339. As a result, the knife support 335 can be detached from the knife head 332. After another knife support 335 is fitted on the knife head 332, the bracket 341 is pivoted inwardly and the screws 342 are tightened to secure the bracket 341 over the notches 339.

In the operation of the purse string suture instrument 200, a plurality of staples 50 are inserted into the staple receiving slots 224 of both staple cartridges 222. Each staple 50 is oriented with its loop 52 received in the notch 261 at the bottom of the staple receiving slot 224 and with its legs 64 and 66 pointing upwardly toward the tissue clamping ridges 253. A single purse string suture 80 is threaded through the loops 52 of all staples 50 in both staple cartridges 222.

After the staples 50 and the purse string suture 80 are loaded into the staple cartridges 222, the jaws 211 and 212 are opened by grasping finger grips 204 and 205 and moving the handles 201 and 202 apart. The instrument 200 is positioned with its opened jaws 211 and 212 on opposite sides of a tubular section of tissue 82. Then, the jaws 211 and 212 are closed by grasping the finger grips 204 and 205 and moving handles 201 and 202 together to clamp the tissue 82 between the cartridges 222 on the jaws 211 and 212. The handles 201 and 202 are latched together by the latch arms 206 and 207 to hold the jaws 211 and 212 closed.

As shown in FIG. 31, the tissue 82 is pinched between the opposed tissue clamping ridges 253 and urged into a slight bulge at the center of each staple cartridge 222. Initially, prior to the actuation of the staple pusher bar 240, the widely spaced vertical surfaces 265 of the pusher bar 240 are located adjacent to the staple legs 64 and 66.

Referring to FIGS. 21 and 22, the staple actuating lever 225 is unlocked by pivoting the locking disc 238 from its upper locked position to its lower unlocked position (shown in phantom lines) engaging finger rest 208. Then, the staple actuating lever 225 is depressed to pivot arm 229 in a clockwise direction about pivot pin 226 and to pull the flexible wire 230 rearwardly. As a result, the connecting wires 234 are pulled rearwardly and each pivot arm 236 (FIG. 27) is pivoted about its pivot screw 242 against the bias of spring 248. The pivotal movement of each pivot arm 236 is transmitted via the pin 243 and slot 244 into longitudinal movement of the staple pusher bar 240 in the direction of arrow A relative to the staple cartridge 222.

Referring to FIG. 28, when the pusher bar 240 is moved in the direction of arrow A, the slanted staple forming edges 264 engage and bend the staple legs 64 and 66 toward each other. As shown in FIG. 32, the tips 68 and 70 of the staple legs 64 and 66 are guided into the tissue 82 between the ridges 253 of the staple cartridge 222. When the pusher bar 240 is fully advanced, the staple legs 64 and 66 are located between the narrowly spaced vertical surfaces 266 of the staple pusher bar 245. Each staple 50 is deformed into the configuration of a figure eight with the staple legs 64 and 66 overlapped to form the loop 84 to secure the staple 50 and the purse string suture 80 to the tissue 82.

When the staple actuating lever 225 is depressed, the staple pusher bars 240 in both staple cartridges are simultaneously actuated. As a result, all of the staples 50 in both cartridges 222 are simultaneously bent to secure the purse string suture 80 to the tissue.

Next, prior to the opening of jaws 211 and 212, the tubular section of tissue 82 is cut crosswise in front of the jaws 211 and 212 by using the knife 320 (FIG. 38). The knife 320 is positioned with its cutting blade 335 adjacent to the front of the purse string suture instrument 200. Then, using the front edges of the jaws 211 and 212 as a guide, the cutting blade 335 is drawn across the front of the purse string suture instrument 200 to cut the tubular section of tissue in the crosswise direction. After the tissue is cut, the handles 201 and 202 are unlatched and moved apart to separate the jaws 211 and 212 and unclamp the tissue. As shown in FIG. 14, the purse string suture 80 remains attached to the tubular section of tissue 82 by a plurality of staples 50. Thereafter, both ends of the purse string suture 80 are pulled to close the tubular section of tissue 82 and the purse string suture 80 is tightened and wrapped about the tubular section of tissue 82. The loops 52 of the staples 50 allow the purse string suture 80 to be moved easily through the staples 50 with minimal resistance or interference from the tissue 82.

Preferably, the purse string suture instrument 200 is a reusable tool constructed of stainless steel. The staple cartridges 222 are one-shot disposable units which are detachable from the jaws 211 and 212 of the instrument. Also, the tissue cutting tool 320 is constructed of stainless steel.

The invention in its broader aspects is not limited to the specific details of the preferred embodiments shown and described, and those skilled in the art will recognize that the invention can be practiced with modification within the spirit and scope of the appended claims.

We claim:

1. A surgical instrument for applying a purse string suture to tissue, comprising:
    a pair of staple cartridges having opposed tissue clamping surfaces for clamping the tissue therebetween;
    a row of staple receiving slots defining an axis formed in each of said cartridges, each slot being able to receive a staple with its legs pointing toward the tissue clamping surface of said cartridge;
    a central slot extending along said tissue clamping surface of each staple cartridge for receiving a purse string suture connected to the staples in each of said staple receiving slots;
    a staple pusher bar slidably mounted in each cartridge and able to engage and bend the legs of each staple toward the tissue clamping surface of said cartridge upon movement of said staple pusher bar relative to said cartridge; and
    actuating means for sliding the pusher bar in each staple cartridge to bend the staple legs and secure the staples and the purse string suture to the tissue clamped between said cartridges wherein:
    said staple pusher bar is movable relative to said cartridge in a direction parallel to the axis of the row of staples therein.

2. The surgical instrument of claim 1, wherein:
    said central slot in each cartridge intersects each of said staple receiving slots therein.

3. The surgical instrument of claim 1, wherein:
    said pusher bar includes a series of opposed pairs of wedge-shaped protrusions corresponding to the staple receiving slots in said cartridge, each pair of wedge-shaped protrusions being adapted to engage and bend the legs of the staple toward the tissue clamping surface into an overlapped configuration when said staple pusher bar is moved longitudinally relative to said cartridge.

4. A surgical instrument of applying a purse string suture to tissue, comprising:
    a plurality of staples, each said staple having a pair of legs;
    a pair of elongated handles pivotally connected together, said handles supporting a pair of jaws for receiving the tissue therebetween;
    a pair of staple cartridges mounted on said jaws, said cartridges having opposed tissue jaws, said cartridges having opposed tissue clamping surfaces for clamping the tissue therebetween;
    a row of staple receiving slots defining an axis formed in each of said cartridges, each slot being able to receive a staple with its legs pointing toward the tissue clamping surface of said cartridge;
    a central slot extending along said tissue clamping surface of each staple cartridge for receiving a purse string suture connected to the staples in each of said staple receiving slots;
    a staple pusher bar slidably mounted in each cartridge and able to engage and bend the legs of each staple toward the tissue clamping surface of said cartridge upon movement of said staple pusher bar in a direction parallel to the axis of said cartridge; and
    actuating means on one of said handles for sliding the pusher bar in each staple cartridge to bend the staple legs and secure the staples and the purse string suture to the tissue clamped between said cartridges.

5. The surgical instrument of claim 4, wherein said actuating means comprises:
    a staple actuating lever pivotally mounted on one of said handles;
    means for connecting said staple actuating lever to the staple pusher bar in each of said cartridges; and
    said staple actuating lever being manually pivotable to displace said connecting means to move the staple pusher bar in each of said cartridges.

6. The surgical instrument of claim 5, which includes:
    a locking member pivotally mounted on one of said handles and movable between a first position in which said staple actuating lever is locked against movement and a second position in which said staple actuating lever is unlocked for movement.

7. A staple cartridge, comprising:
    a plurality of staples, each said staple having a pair of legs;
    an elongated housing including a tissue engaging surface, a plurality of transverse slots extending into said housing from said tissue engaging surface for receiving said staples therein, and an elongated central slot for receiving a purse string suture attached to each of the staples, said central slot extending longitudinally along said housing and intersecting said transverse slots; and a staple pusher bar slidably mounted for longitudinal movement in said housing, said staple pusher bar being able to engage and bend the legs of each staple toward the tissue clamping surface to secure the staples and the purse string suture to the tissue.

8. The staple cartridge of claim 7, wherein:

said pusher bar includes a series of opposed pairs of wedge-shaped protrusions corresponding to the staple receiving slots formed in said housing, each pair of wedge-shaped protrusions being able to engage and bend the legs of the staple toward the tissue clamping surface into an overlapped configuration when said staple pusher bar is moved longitudinally relative to said housing.

9. The staple cartridge of claim 8, wherein:

each wedge-shaped protrusion has a staple forming edge slanted inwardly toward the center of said staple pusher bar for engaging and bending the staple legs inwardly toward each other as said staple pusher bar is moved relative to said cartridge.

10. The staple cartridge of claim 7, wherein:

each staple receiving slot is located between a pair of ridges which extend upwardly from the top of the housing.

11. The staple cartridge of claim 10, wherein:

each pair of ridges is separated by a depression from the next adjacent pair of ridges.

12. The staple cartridge of claim 10, wherein:

said elongated central slot opens into a longitudinal V-shaped groove defined by inclined surfaces which are sloped upwardly and outwardly from the central slot and terminate at the top of said ridges.

13. The staple cartridge of claim 7, wherein:

each staple includes an eyelet which extends in the opposite direction from the staple legs for receiving the purse string suture; and said housing includes a plurality of recesses at the bottom of said staple receiving slots for receiving the eyelets of the staples therein.

14. A surgical staple for securing a purse string suture to tissue, comprising:

a staple body shaped into a ring to provide an eyelet for receiving a purse string suture, said staple body including two or more legs with barbed ends for anchoring said legs to the tissue wherein:

said legs are bent alternately forward and rearward relative to said ring.

15. The staple of claim 14, which includes:

a plurality of legs extending in a fan-like configuration from said staple body.

16. A method for securing a purse string suture to a tubular section of tissue, comprising:

positioning a plurality of staples about the periphery of a tubular section of tissue, each of said staples including an eyelet for receiving the purse string suture;

threading the purse string suture through the eyelets of said staples to attach the purse string suture to the staples; and driving the staples into the tissue to secure the purse string suture thereto.

17. A method for securing a purse string suture to a tubular section of tissue, comprising:

positioning a plurality of staples about the periphery of a tubular section of tissue, each of said staples including a loop for receiving the purse string suture and a pair of deformable legs;

threading the purse string suture through the loops of each staple; and deforming the staple legs into an overlapping configuration to form another loop extending into the tissue to secure the staples and the purse string suture to the tissue.

* * * * *